United States Patent [19]
Theriot et al.

[11] Patent Number: 5,329,054
[45] Date of Patent: Jul. 12, 1994

[54] DECARBOXYLATION PROCESS

[75] Inventors: Kevin J. Theriot; Niomi L. Krzystowczyk; Yueh-Dong Chen; Edward A. Burt; Lawrence H. Shepherd, Jr., all of Baton Rouge, La.

[73] Assignee: Albemarle Corporation, Richmond, Va.

[21] Appl. No.: 93,166

[22] Filed: Jul. 19, 1993

[51] Int. Cl.$^5$ .................. C07C 17/24; C07C 17/33; C07C 25/13; C07C 25/02
[52] U.S. Cl. .................. 570/142; 558/411; 560/103; 562/41; 562/479; 564/281; 564/391; 568/314; 568/932; 568/939; 570/190
[58] Field of Search .................. 570/142, 190; 562/479, 562/41; 568/314, 932, 939; 564/281, 391; 558/411; 560/103

[56] References Cited

U.S. PATENT DOCUMENTS

| 2,439,237 | 9/1948 | Carr | 562/479 |
| 2,729,674 | 1/1956 | McKinnis | 562/479 |
| 3,210,415 | 10/1965 | Berkey et al. | 562/479 |
| 3,257,420 | 6/1966 | Szarvasi et al. | 562/479 |
| 4,782,180 | 11/1988 | Wemple et al. | 562/479 |

FOREIGN PATENT DOCUMENTS

| 6425737 | 1/1989 | Japan . | |
| 818434 | 8/1959 | United Kingdom | 562/479 |
| 2122190 | 1/1984 | United Kingdom . | |

OTHER PUBLICATIONS

Sartoni, et al. Chem. Ber. 100, 3016–3023 (1967).
Burdon, et al, J. Chem. Soc. 6336–6342 (1965).

Primary Examiner—Joseph E. Evans
Attorney, Agent, or Firm—David M. Bunnell

[57] ABSTRACT

Activated carboxylic acids and esters such as pentafluorobenzoic acid are rapidly decarboxylated in high yields by reacting the acid or ester with an alkanolamine reagent which catalyzes the reaction.

11 Claims, No Drawings

DECARBOXYLATION PROCESS

The invention relates generally to the decarboxylation of carboxylic acids and more particularly to a process for the decarboxylation of activated carboxylic acids and esters, such as pentafluorobenzoic acid, using an alkanolamine reagent to catalyze the reaction.

Activated carboxylic acids, such as pentafluorobenzoic acid or tetrafluorophthalic acid, can be thermally decarboxylated by heating at a temperature of 340° C., as is reported by P. Sartoni et al. in *Chem. Ber.* 100, 3016-3023 (1967). They can also be decarboxylated by heating the acid in the presence of a base, such as aqueous $NH_3$ (see J. Burdon et al. *J. Chem. Soc.*, 6336-6342 (1965)) or a non-polycyclic organic base, such as $[Me(CH_2)_7]_3N$ (see Niizeki et al. *Chem. Ab.*, Vol 111, 96836m, 702 (1989)). Such processes either proceed slowly and/or give products in low yields. Maximum yields, in any event, are about 70 mole %. British Patent Application 2,122,190 discloses the decarboxylation of halogenated benzoic acids and esters using a solvent and, preferably, a polar, aprotic solvent.

A decarboxylation process has now been discovered which is rapid, provides high yields, and can be conducted with a reduced amount of catalytic reagent and at relatively low temperatures.

In accordance with this invention there is provided a process for the decarboxylation of an activated carboxylic acid or ester, said process comprising reacting said acid or ester with an alkanolamine reagent so as to remove the carboxylic acid or ester group from said acid or ester and replace said carboxylic acid or ester group with hydrogen.

By "activated carboxylic acid or ester" is meant that the acid or ester contains one or more electron withdrawing moieties (i.e. an atom or group) but which will not undergo any significant side reactions with the alkanolamine reagent. Non-limiting examples of such election withdrawing moieties include halogen, $NR_3^+$, $CF_3$, $NO_2$, COOR, COR, $SO_3$, CN and the like, where R is H, or an alkyl or aryl group having up to about 30 carbon atoms. For the activation of aryl carboxylic acids or esters, the electron withdrawing atom or group should be located at one or more of the ortho or para positions on the ring (i.e. a location which would normally activate the aromatic ring towards nucleophilic aromatic substitution). Non-limiting examples of activated carboxylic acids include, pentafluorobenzoic acid, tetrafluorophthalic acid, tetrafluoroterphthalic acid, 2,4-dinitrobenzoic acid, o-nitrobenzoic acid, o-fluorobenzoic acid, p-fluorobenzoic acid, pentachlorobenzoic acid, p-trifluoromethylbenzoic acid, p-cyanobenzoic acid, o-acetylbenzoic acid, p-acetylbenzoic acid, 2,4,6-trifluorobenzoic acid, p-trimethylaminobenzoic acid and the like. The carboxylic esters are, preferably, lower alkyl ($C_1$ to $C_6$) esters of such activated acids.

The decarboxylated products produced by the process of the invention are useful chemical intermediates, for example, in making pharmaceutical, agrochemical, optical and catalyst compositions.

The alkanolamine reagents for use in the process contain one or more, and preferably two hydroxyl groups. Non-limiting examples of suitable alkanolamine reagents include ethanolamine, diethanolamine, triethanolamine, 2-amino-2-hydroxylmethyl-1,3-propanediol, 2-amino-2-methylpropanol 2-amino-1,3-propanediol, 3-amino-1-propanol, and the like.

Preferably, the amine reagent is present in the reaction mixture in at least a slight molar excess relative to the acid. Preferred amounts are from about 1.05 to 3 or more moles of amine reagent per mole of carboxylic acid. It has been found that by continuously (or incrementally) adding the acid to a reactor containing the heated amine, such that the amine remains in molar excess in the reactor, while distilling off the decarboxylated product, less than a molar equivalent of amine (for example, about 0.5 molar equivalent) to the total amount of moles of acid to be decarboxylated can be used. This is because the amine reagent is apparently not consumed to any major degree in the reaction. By melting the acid and slowly feeding it to the reaction zone as a liquid over a long period of time, product yields and purity are improved.

The reaction temperature is readily selected to obtain the optimum yield in a reasonable reaction time for any particular reagent and acid. The initial reaction may be exothermic. The major by-product of the reaction is carbon dioxide. Generally, reaction temperatures of from about 50° to 200° C. and, preferably, from about 80° to 130° C. are suitable. The reaction can be carried out without a solvent. Optionally, sufficient water can be added to dissolve the amine reagent. However, the presence of water can lead to undesirable byproducts.

The invention is further illustrated by, but is not intended to be limited to, the following examples.

EXAMPLE 1

Pentafluorobenzoic acid (3.00 grams 14.2 mmol) 2-amino-2-hydroxymethyl-1,3-propanediol (3.44 grams 28.4 mmol), which provided an amine to acid mole ratio of 2:1, and sufficient water to dissolve the amine (about 7 mL) were heated in a sealed Fisher-Porter tube for 20 hours at a temperature of 140° C. The reactor was then cooled and the bottom product layer was separated. The yield of pentafluorobenzene was 78%. The purity of the product as determined by G.C. was >99.8%.

EXAMPLE 2

Pentafluorobenzoic acid (3.00 grams 14.2 mmol) and 2-amino-2-hydroxymethyl-1,3-propanediol (1.83 grams 15.1 mmol), which provided an amine to acid mole ratio of 1.06:1, were heated in a sealed tube. No water was added. The heating time was 4 hours and the temperature was 155° C. The yield of pentafluorobenzene was 69% and the purity of the product as determined by G.C. was >99.8%.

EXAMPLE 3

Pentafluorobenzoic acid (5.00 grams 23.6 mmol) and 2-amino-2-hydroxymethyl-1,3-propanediol (3.00 grams 24.8 mmol), which provided an amine to acid mole ratio of 1.05:1, were heated in a distillation apparatus at from 164°-168° C. for 30 minutes. The product pentafluorobenzene was collected overhead as a colorless liquid. The yield was 79%.

EXAMPLE 4

The process of Example 3 was repeated except that diethanolamine was used as the alkanolamine reagent in an amine to acid mole ratio of 1.05:1. The reaction temperature (the initial mixing of the reactants was exothermic) ranged from 135° C. to 145° C. The yield of 98% pure pentafluorobenzene was 85%.

EXAMPLE 5

Diethanolamine (68.03 Kg) is charged to a stirred reactor. Pentafluorobenzoic acid (182 Kg) is melted (mp 105° C.) and slowly fed to the reactor. Product pentafluorobenzene and carbon dioxide are generated and are flashed overhead. The product is condensed and collected. The reaction is exothermic and rapidly builds pressure as the by-product carbon dioxide is produced. The reaction temperature is controlled at from about 100° C. to 115° C. during the addition of the acid. The addition rate is from about 0.2 to 1 Kg/minute. After all the acid is added, which typically takes about 4 to 5 hours, the reactor temperature is raised to about 130° C. to distill the remaining product from the reactor. The product pentafluorobenzene yield is about 85%. Preferred acid feed temperatures are about 120° C. and preferred acid feed rates are about 0.5 to 0.6 Kg/minute.

What is claimed is:

1. A process for the decarboxylation of an activated carboxylic acid or ester, said process comprising reacting said acid or ester with an alkanolamine reagent so as to remove the carboxylic acid or ester group from said acid or ester and replace said carboxylic acid or ester group with hydrogen, said carboxylic acid or ester being continuously or incrementally added to said alkanolamine reagent over a period of time such that said alkanolamine reagent remains in molar excess to said carboxylic acid or ester in the reaction mixture, and the decarboxylated product and carbon dioxide being continually removed as a vapor from the reaction mixture.

2. The process of claim 1 wherein the mole ratio of said alkanolamine reagent to said carboxylic acid or ester is from about 1.05 to 3.

3. The process of claim 1 wherein the reaction temperature is from about 80° to 130° C.

4. The process of claim 1 wherein the reaction temperature is from about 50° to 200° C.

5. The process of claim 1 wherein said activated carboxylic acid or ester is an aryl carboxylic acid or ester which is substituted in at least one ortho or para position in the aromatic ring with an election withdrawing moiety.

6. The process of claim 5 wherein said electron withdrawing moiety is selected from the group consisting of halogen, $NR_3^+$, $CF_3$, $NO_2$, $COOR$, $COR$, $SO_3$ and $CN$, where R is H, or an alkyl or aryl group having up to about 30 carbon atoms.

7. The process of claim 8 wherein said aryl carboxylic acid is pentafluorobenzoic acid.

8. The process of claim 7 wherein said alkanolamine reagent is diethanolamine.

9. The process of claim 7 wherein said alkanolamine reagent is 2-amino-2-hydroxymethyl-1,3-propanediol.

10. The process of claim 7 wherein said alkanolamine reagent is triethanolamine.

11. The process of claim 1 wherein said carboxylic acid or ester is melted and added to the alkanolamine reagent in liquid form.

* * * * *